US00PP32986P2

(12) United States Plant Patent
Hansen

(10) Patent No.: US PP32,986 P2
(45) Date of Patent: Apr. 20, 2021

(54) ***ACHILLEA* PLANT NAMED 'FIREFLY DIAMOND'**

(50) Latin Name: ***Achillea* hybrid**
Varietal Denomination: Firefly Diamond

(71) Applicant: Hans A Hansen, Zeeland, MI (US)

(72) Inventor: Hans A Hansen, Zeeland, MI (US)

(73) Assignee: Walters Gardens, Inc., Zeeland, MI (US)

( * ) Notice: Subject to any disclaimer, the term of this patent is extended or adjusted under 35 U.S.C. 154(b) by 0 days.

(21) Appl. No.: 16/602,656

(22) Filed: Nov. 15, 2019

(51) Int. Cl.
*A01H 5/02* (2018.01)
*A01H 6/14* (2018.01)

(52) U.S. Cl.
USPC ..... Plt./263.1

(58) Field of Classification Search
USPC ..... Plt./263.1
CPC ... A01H 5/02; A01H 5/00; A01H 6/14; A01H 6/04; A01H 6/06
See application file for complete search history.

(56) References Cited

PUBLICATIONS

Four Star Plugs & Liners from Four Star, Michigan 2019 retrieved on May 18, 2020, retrieved from the Internet at https://cdn.shopify.com/s/files/1/1537/5553/files/2020FourStarPriceList.pdf, pp. 1-2,13. (Year: 2019).*

* cited by examiner

*Primary Examiner* — June Hwu

(57) ABSTRACT

A new and distinct Yarrow, *Achillea* plant named 'Firefly Diamond', with narrow, green, fern-like foliage; tall, stiff, heavily branched stems with white ray florets in large cymes, beginning in late June and continuing for about seven weeks and repeating if deadheaded. The new plant is useful for landscaping, as a specimen or en masse and as a cut flower.

1 Drawing Sheet

Botanical designation: *Achillea* hybrid.
Cultivar denomination: 'Firefly Diamond'.

STATEMENT REGARDING PRIOR DISCLOSURES UNDER 37 CFR 1.77(b)(6)

The first public disclosure of the claimed plant, in the form of a sale, was made by Walters Gardens, Inc. on Apr. 1, 2019. Prior to that, on Dec. 1, 2018 the claimed plant was displayed as a photograph with a brief description on a website operated by Walters Gardens, Inc., followed by listing with a photograph and brief description in the Walters Gardens 19-20 Catalog circulated on May 29, 2019. Walters Gardens, Inc. obtained the plant and all information relating thereto, from the inventor. No plants of *Achillea* 'Firefly Diamond' have been sold, in this country or anywhere in the world, nor has any disclosure of the new plant been made, more than one year prior the filing date of this application, and such sale or disclosure within one year was either derived directly or indirectly from the inventor.

BACKGROUND OF THE PLANT

The present invention relates to the new and distinct yarrow herein also referred to as *Achillea* 'Firefly Diamond', by the cultivar name, 'Firefly Diamond', or as the new plant. The new plant was selected by the inventor as a single seedling resulting from a self-pollination of a proprietary, unreleased, unnamed seedling known only by the breeder code 13-5-8 (not patented) in research facility of a wholesale perennial grower based in Zeeland, Mich., USA. The cross was performed on Jun. 23, 2014 and the seeds from this cross were collected on Sep. 23, 2014. The single seedling was then isolated and compared in subsequent years to other Yarrow and subsequently found to be different from all cultivars known to the discoverer and eventually given the breeder code 14-23-1.

Asexual propagation at the same nursery in Zeeland, Mich., USA by shoot tip cuttings and division since August of 2016 has shown 'Firefly Diamond' to be stable and reproduce true to type in successive generations.

SUMMARY OF THE PLANT

*Achillea* 'Firefly Diamond' has not been observed in all possible environmental conditions. The phenotype may vary slightly with changes in environments such as light intensity, fertility, water availability, etc. without, however any variation in genotype.

*Achillea* 'Firefly Diamond' is distinct from all cultivars known to the inventor in the following traits:

1. Mounded habit about 70 cm tall and 100 cm wide;
2. Green finely-dissected foliage;
3. Heavily-branched compound corymbs with broad clusters of inflorescences;
4. White ray florets remain effective throughout the flowering period;
5. Sturdy stems withstand wind and rain;
6. Long flowering period beginning late June and continuing for about seven weeks;
7. Repeat flowering if deadheaded.

Plants of *Achillea* 'Firefly Diamond' are most similar to 'Balvinwite' U.S. Plant Pat. No. 25,711 and 'Peter Cottontail' U.S. Plant Pat. No. 31,756. 'Balvinwite' is smaller in habit, both shorter and narrower than the new plant. 'Peter Cottontail' is slightly smaller in habit, the inflorescences and ray florets are much larger on cymes that are more full and rounded, and the foliage is not as dissected. Photographs or plants of the parent selection were not maintained, so no comparison with the parents are possible.

BRIEF DESCRIPTION OF THE DRAWINGS

The color drawings illustrate the overall characteristics of *Achillea* 'Firefly Diamond' as a two-year-old plant in a full-sun trial garden in Zeeland, Mich. The colors are as true as reasonably possible given the technology available. The color values may vary slightly depending on light intensity and quality.

DETAILED BOTANICAL DESCRIPTION

Figure 1:
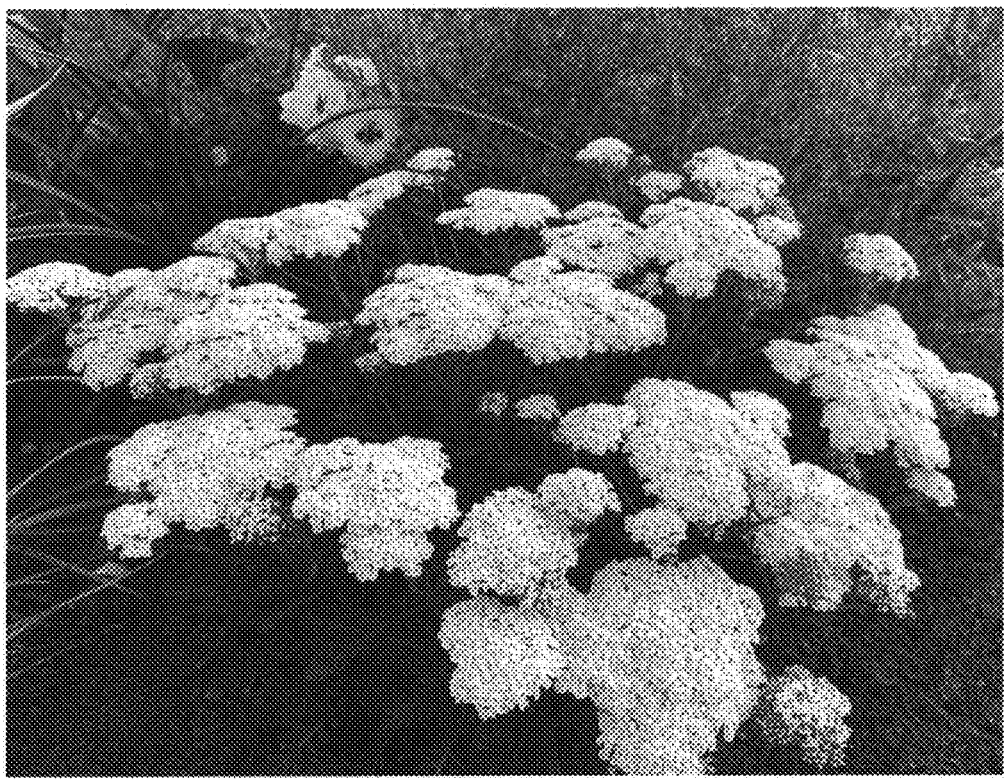
FIG. 1 shows the new plant in a trial facility.
Figure 2:
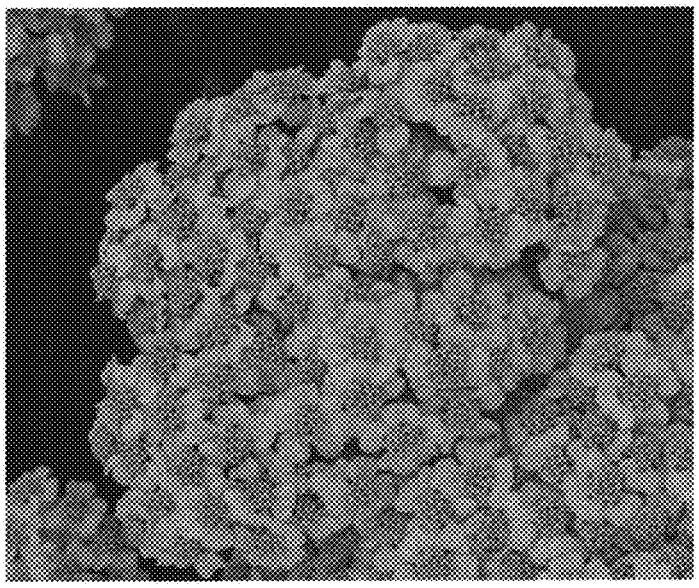
FIG. 2 shows a close-up of the inflorescence of the new plant.

The following description of the new plant is based on a three-year-old plant growing in a full-sun trial garden in Zeeland, Mich., USA. Environmental conditions for the growing season daytime temperatures range between 12-30° C., and night temperatures range between 6-19° C. Except for ordinary dictionary color usage, color references are according to The Royal Horticultural Society Colour Chart, 2015 edition.

Parentage: Female or seed parent 13-5-8; male or pollen parent 13-5-8;

Asexual propagation: Shoot tip cuttings, about 10 to 14 days to initiate roots; time to finish as #1 field grown size about 9 months;

Plant habit: Dense axillary branches; upright, heavily-branched, herbaceous, winter-hardy, perennial mound; up to 70.0 cm tall and 100.0 cm wide; average about 64.0 cm tall and about 83.0 cm across;

Leaves: Alternate; canescent; pinnatisect with lobules incised to midrib; lanceolate; acute apex; base attenuate; except proximal leaves; micro-lanulose abaxial and glabrous adaxial; up to about 30.0 cm long and about 4.5 cm wide with individual lobes to about 28.0 mm long and about 14.0 mm wide; average leaf size about 17 cm long and 3.0 cm wide;

Leaf color: Young expanding leaves adaxial lobes nearest RHS 137B and midrib nearest RHS 138B, abaxial lobes nearest RHS 137B and midrib nearest RHS 138B; mature leaves adaxial lobes nearest RHS 137A and midrib nearest RHS 148D, abaxial lobes nearest RHS 138A and midribs nearest RHS 148D;

Foliage fragrance: Slightly herbal;

Veins: Pinnate; only adaxial and abaxial midrib obvious; abaxial midrib costate, adaxial midrib flat; adaxial sparsely lanulose, abaxial lanulose;

Petiole: Channeled; lanulose; to 4.0 cm long and 4.0 mm wide at base; color nearest RHS 147C;

Stems: Upright; cylindrical; lanulose to micro-pubescent; longitudinally ridged in distal portion; color nearest RHS 137B proximally, distally striped RHS 137B and RHS 191B; flowering in upper 9.0 cm and 15 cm across; branches to about 15.0 cm long and 3.0 mm diameter at base;

Inflorescence: Individual inflorescence about 6.0 mm diameter, about 7.0 mm tall from bottom of involucral bracts to top of center disk tepals; disk about 3.0 mm across; attitude mostly upright; producing branched stems with about 500 inflorescences per stem; branched panicle average size about 15.0 cm across, flowering in upper 9.0 cm and 15 cm across; branches to about 15.0 cm long and 3.0 mm diameter at base;

Receptacle: About 3.0 mm tall and 2.0 mm across; color nearest RHS 148D;

Inflorescence fragrance: Not detected;

Phyllaries: About 16 in two whorls; lanceolate; acute apex; truncate base; margin entire and ciliolate; outer or lower set about 2.0 mm long and 1.0 mm across, inner set about 3.5 mm long and 2.0 mm across; glabrous adaxial, puberulent abaxial; tightly adpressed against ray petals;

Phyllary color: Adaxial and abaxial nearest RHS 137B with midrib and margin nearest RHS 155C;

Bristles: Membranous; numerous; about 3.0 mm long and 0.5 mm across; color nearest RHS 152D;

Flowering period: Late June, for about 7 weeks and repeating if deadheaded;

Flower longevity: 4 to 6 days;

Inflorescence buds: With ray florets still erect 6.0 mm tall and 3.5 mm across; ovoid;

Inflorescence bud color: Ray florets while still upright exposed abaxial petal color nearest RHS NN155D; phyllaries color nearest RHS 137B with midrib and margin nearest RHS 155C;

Pedicel: Cylindrical; lanulose; strong; upright attitude; heavily branched; up to 5.0 mm long and 0.7 mm diameter; average 4.0 mm long; and 0.5 mm diameter;

Pedicel color: Color nearest RHS 138B;

Ray florets: Imperfect; pistillate; typically about five per inflorescence; with style about 2.5 mm long and split stigma;

Ray floret ligule: Rounded with basal claw; apex rounded, emarginate with two notches about 0.5 mm deep, margin entire; base claw, attenuate; opening to a 90° angle; glabrous adaxial and adaxial; about 5.5 mm long and about 3.5 mm wide; basal claw about 2.0 mm long and about 1.0 mm across;

*Young ray floret ligule color when first flat*.—Adaxial nearest RHS NN155D, abaxial nearest RHS N155D and claw base nearest RHS 138B.

*Mature ray floret ligule color*.—Adaxial nearest RHS NN155D; abaxial nearest RHS NN155D with claw nearest RHS 138B.

*Ray floret ligule color before dehiscing*.—Adaxial nearest RHS NN155D; abaxial nearest RHS NN155D with claw nearest RHS 138B.

*Style*.—Cylindrical; about 2.0 mm long and 0.2 mm diameter; exserted; color nearest RHS 155C.

*Stigma*.—Bifid; about 0.5 mm long and 0.2 mm diameter; color nearest RHS 155B.

Disk florets: About 16 per capitulum; tubular; glabrous; consisting of five tepals, staminal tube and pistil; size about 4.0 mm long by 1.0 mm wide at apex;

*Tepals*.—Five; linear; fused in basal 2.5 mm; apex acute; margin entire; 3.0 mm long and 0.5 mm wide at fusion.

*Tepal color*.—Initially nearest RHS 193D adaxial and abaxial; at maturity nearest RHS 157D.

*Staminal tube*.—Made up of five adnate stamens; about 2.0 mm long.

*Filaments*.—Cylindrical; about 0.5 mm long and 0.1 mm diameter; color nearest RHS NN155A.

*Anther*.—About 1.0 mm long; color nearest RHS N187C.

*Pollen*.—Fine, round, closest to RHS 11D.

*Style*.—Bifid; cylindrical; exserted; about 2.0 mm long and 0.2 mm diameter; color nearest RHS N155D.

*Stigma*.—Bifid; reflexing as it matures; about 0.5 mm long; color nearest RHS 155D.

Seed: Flattened deltoid; acute apex and truncate base; surface glabrous; about 2.0 mm long and 0.7 mm across base; Seed color: Between RHS 165A and RHS 165B in center and RHS 161D around edges;

*Achillea* 'Firefly Diamond' is tolerant of winter temperatures as low as −35° C. and summer temperatures as high as 38° C. It is not known to be tolerant of diseases and pest that are common to other *Achillea* cultivars.

I claim:

1. A new and distinct cultivar of *Achillea* plant named 'Firefly Diamond' as described and illustrated.

* * * * *